(12) United States Patent
Gordon

(10) Patent No.: US 7,648,465 B2
(45) Date of Patent: Jan. 19, 2010

(54) METHOD OF TESTING A SURGICAL SYSTEM

(75) Inventor: Raphael Gordon, San Dimas, CA (US)

(73) Assignee: Alcon, Inc., Hunenburg (CH)

( * ) Notice: Subject to any disclaimer, the term of this patent is extended or adjusted under 35 U.S.C. 154(b) by 655 days.

(21) Appl. No.: 11/168,836

(22) Filed: Jun. 28, 2005

(65) Prior Publication Data

US 2007/0010730 A1 Jan. 11, 2007

(51) Int. Cl.
*A61B 10/00* (2006.01)
*A61B 3/16* (2006.01)
(52) U.S. Cl. .................. 600/562; 600/399; 600/401
(58) Field of Classification Search .......... 600/561, 600/398, 399, 400, 401, 402, 403; 604/31, 604/67, 151
See application file for complete search history.

(56) References Cited

U.S. PATENT DOCUMENTS

| 3,589,363 | A | 6/1971 | Banko et al. |
|---|---|---|---|
| 4,041,947 | A | 8/1977 | Weiss et al. |
| 4,223,676 | A | 9/1980 | Wuchinich et al. |
| 4,246,902 | A | 1/1981 | Martinez |
| 4,493,694 | A | 1/1985 | Wuchinich |
| 4,515,583 | A | 5/1985 | Sorich |
| 4,548,205 | A | 10/1985 | Armeniades et al. |
| 4,589,415 | A | 5/1986 | Haaga |
| 4,609,368 | A | 9/1986 | Dotson, Jr. |
| 4,722,350 | A | 2/1988 | Armeniades et al. |
| 4,841,984 | A | 6/1989 | Armeniades et al. |
| 4,869,715 | A | 9/1989 | Sherburne |
| 4,922,902 | A | 5/1990 | Wuchinich et al. |
| 4,989,583 | A | 2/1991 | Hood |
| 4,998,914 | A | 3/1991 | Wiest et al. |
| 5,154,694 | A | 10/1992 | Kelman |
| 5,267,956 | A | 12/1993 | Beuchat et al. |
| 5,359,996 | A | 11/1994 | Hood |
| 5,364,342 | A | 11/1994 | Beuchat et al. |
| 5,494,530 | A | 2/1996 | Graf |
| 5,499,969 | A | 3/1996 | Beuchat et al. |
| 5,556,378 | A | 9/1996 | Storz et al. |
| 5,586,973 | A | 12/1996 | LeMaire et al. |
| 5,609,576 | A * | 3/1997 | Voss et al. ............. 604/67 |
| 5,899,674 | A | 5/1999 | Jung et al. |
| 6,293,926 | B1 | 9/2001 | Sorensen et al. |
| 6,875,194 | B2 | 4/2005 | MacKool |
| 6,986,753 | B2 | 1/2006 | Bui |
| 2002/0019607 | A1* | 2/2002 | Bui ..................... 604/67 |
| 2003/0190244 | A1 | 10/2003 | Davis et al. |
| 2004/0089080 | A1 | 5/2004 | Kadziauskas et al. |
| 2004/0167462 | A1 | 8/2004 | MacKool |
| 2004/0187613 | A1 | 9/2004 | Peacey et al. |
| 2005/0080375 | A1 | 4/2005 | Kadziauskas et al. |
| 2006/0058811 | A1 | 3/2006 | Kishimoto et al. |
| 2007/0010730 | A1 | 1/2007 | Gordon |

(Continued)

OTHER PUBLICATIONS

Initial Publication without International Search Report for PCT/US2006/023656, Publication No. WO2007/001929, 12 pages.

(Continued)

*Primary Examiner*—Max Hindenburg
*Assistant Examiner*—Adam J Eiseman
(74) *Attorney, Agent, or Firm*—Russell Henrichs

(57) ABSTRACT

A method for direct indication of the IOP level without requiring an additional pressure transducer being introduced into the irrigation path. The method of the present invention estimates resistance ratio for a particular setup, and thus does not assume a typical value; the estimation is performed in a pre-operational configuration that is the closest possible to the surgical configuration.

11 Claims, 2 Drawing Sheets

U.S. PATENT DOCUMENTS

2008/0006096 A1    1/2008   Gordon et al.
2008/0033349 A1    2/2008   Suzuki

OTHER PUBLICATIONS

Later Publication of International Search Report for PCT/US2006/023656, Publication No. WO2007/001929, 2 pages.

Initial publication without International Search Report for PCT/US2006/023145, Publication No. WO2007/001859, 20 pages.

Later Publication of International Search Report for PCT/US2006/023145, Publication No. WO2007/001859, 2 pages.

Supplementary European Search Report for Application No. EP 06 78 5059, Publication No. 1895958, 2 pages.

* cited by examiner

METHOD OF TESTING A SURGICAL SYSTEM

BACKGROUND OF THE INVENTION

This invention relates generally to the field of cataract surgery and more particularly to an intraoperative pressure monitoring method for use with a phacoemulsification system.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens.

A typical ultrasonic surgical device suitable for ophthalmic procedures consists of an ultrasonically driven handpiece, an attached cutting tip, and irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece by flexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve.

In use, the ends of the cutting tip and irrigating sleeve are inserted into a small incision of predetermined width in the cornea, sclera, or other location. The cutting tip is ultrasonically vibrated along its longitudinal axis within the irrigating sleeve by the crystal-driven ultrasonic horn, thereby emulsifying the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the cutting tip and horn bores and the aspiration line and into a collection device. The aspiration of emulsified tissue is aided by a saline flushing solution or irrigant that is injected into the surgical site through the small annular gap between the inside surface of the irrigating sleeve and the cutting tip.

During cataract surgery, it is necessary to control the intraocular pressure ("IOP") within the eye. Lack of control over the IOP may impair the effectiveness or ease of the procedure, and in certain cases may result in damage to tissue, such are the result of a collapse of the eyeball with concomitant tissue damage. Conversely, over-pressuring the intraocular region may also result in damage to the sensitive retinal, optic nerve, or corneal tissue. However, it is occasionally desirable to apply controlled high pressure for a brief time period, for example, to staunch bleeding in the intraocular region.

One method of controlling pressure within the eye during surgery is disclosed in U.S. Pat. No. 4,041,947 to Weiss, et al. That patent discloses the use of limiting valves external to the eye on the infusion and aspiration lines. These limiting valves are designed to provide pressure relief if either the pressure in the infusion line exceeds a high limit, or if the pressure in the aspiration line exceeds a low limit. This device does provide some ability to maintain pressure within a predetermined range of values, but does not allow the surgeon to accurately know or set the IOP.

IOP can be directly measured by insertion of a pressure transducer into the eye. U.S. Pat. Nos. 4,548,205, 4,722,350, and 4,841,984 to Armeniades, et al., disclose direct measurement and control of the IOP. A pressure transducer is inserted into the eye as an independent tool or integrated into the cutting tool. Alternatively, a pressure transducer can be integrated into a separate tool that provides infusion or aspiration. However, there are several problems with tools which provide direct measurement of the IOP. If the pressure transducer is incorporated into the invasive portion of a tool, the tool must be made larger in diameter than is necessary to perform the actual surgery. This approach requires a correspondingly larger incision in the eyeball for tool insertion. Further, integration of a pressure transducer into another tool creates inaccuracies in the pressure readings caused by the proximity of the transducer to the operating infusion line, aspiration line, or surgical tool.

One solution to the size problem is to design a tool with a channel which is inserted into the eye and which provides fluid communication with a pressure transducer outside of the eye. However, this design suffers from the same accuracy problems detailed above, as well as problems caused by debris from the operation clogging the channel. This accuracy problem can be overcome by providing a separate tool that only contains a pressure transducer for insertion into the eye away from the operating tools. However, this approach is disfavored because it requires another incision into the eye.

Currently, no commercial surgical console provides any direct indication of the IOP level. Users control IOP by adjusting the irrigation source pressure (bottle height) to the level appropriate for combination of the settings used (aspiration rate, vacuum limit, tip, sleeve, etc.). Users evaluate and establish a certain IOP level based on their experience with a particular instrument. Although one commercially available surgical instrument, the INFINITI® Vision System, has an irrigation pressure sensor ("IPS") that can be used as an indirect indicator of the IOP quality, the variables downstream of the sensor can distort the interpretation of the IPS reading. For example, given identical instrument setting, a more restrictive irrigation sleeve will result in a higher IPS reading, which can be misinterpreted as indicating a higher IOP level, whereas in reality the IOP will be lower than expected.

Therefore, a need continues to exist for a method of measuring IOP during ophthalmic surgery.

BRIEF SUMMARY OF THE INVENTION

The present invention improves upon the prior art by providing a method for direct indication of the IOP level without requiring an additional pressure transducer being introduced into the irrigation path. The method of the present invention estimates resistance ratio for a particular setup, and thus does not assume a typical value; the estimation is performed in a pre-operational configuration that is the closest possible to the surgical configuration. Although the method accuracy is affected by a variable that can not be evaluated in pre-op tests, i.e. incision/irrigation sleeve interface (namely how tight/loose the incision is), the estimated value can still be the closest direct IOP indication available, and can be interpreted as the best case IOP.

Accordingly, one objective of the present invention is to provide a surgical console control system.

Another objective of the present invention is to provide a surgical console control system having a method for determining IOP.

Another objective of the present invention is to provide a method for estimating the fluid resistance ratio for a particular setup.

These and other advantages and objectives of the present invention will become apparent from the detailed description and claims that follow.

DETAILED DESCRIPTION OF THE INVENTION

The inventor has discovered that the changes in irrigation and aspiration pressure during the priming cycle of a surgical system can be used to estimate the flow resistance in the system. Once the approximate flow resistance is known, that information can be used to estimate the pressure within the system and, as a consequence, the pressure at the operative site.

Figure 1:
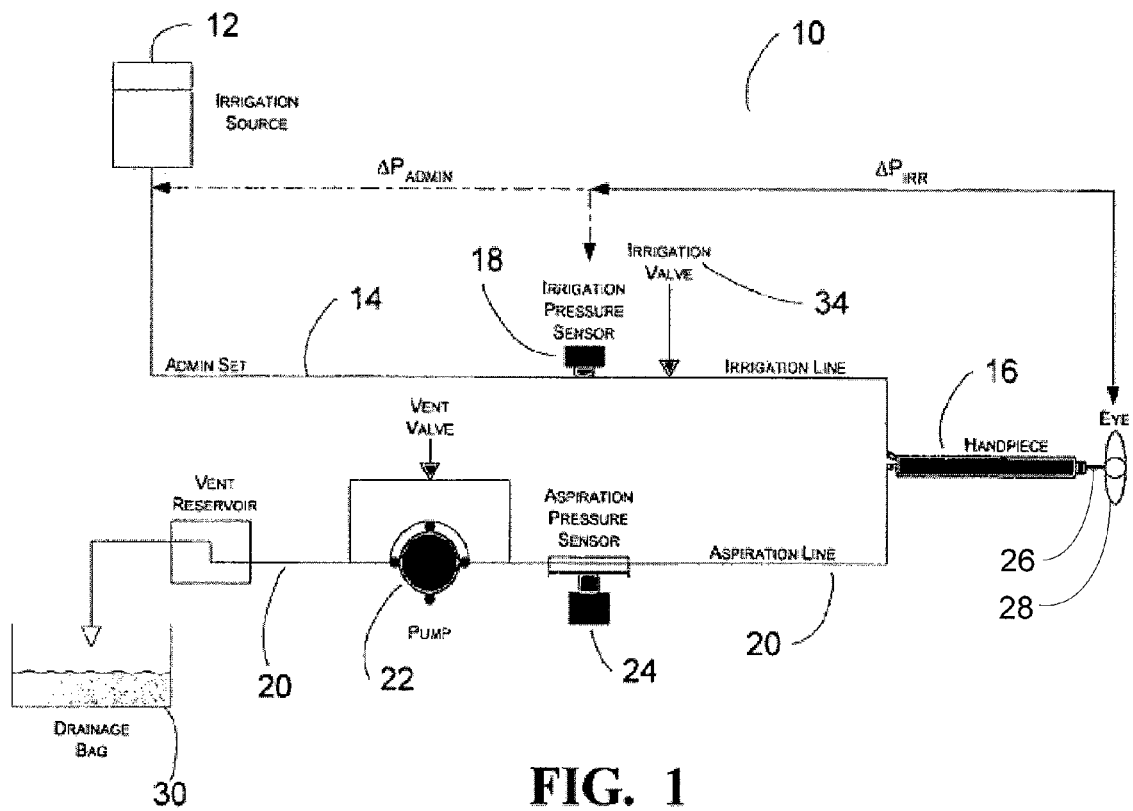
FIG. 1 is a block diagram of one embodiment of a control system that can be used with the method of the present invention during surgery.

As best seen in FIG. 1, system 10 of the present invention generally includes pressurized source of irrigation fluid 12, irrigation line 14 running from source 12 to handpiece 16, irrigation pressure sensor ("IPS") 18, aspiration line 20 running from handpiece 16, pump 22 for providing a vacuum to aspiration line 20 and aspiration pressure (vacuum) sensor 24. During surgery, tip 26 on handpiece 16 is held within eye 28 so that there is continuous fluid communication from irrigation source 12 to drainage bag 30 through irrigation line 14, handpiece 16, aspiration line 20 and pump 22. The fluid resistance in this continuous path is unknown, because of the various combinations of sleeves, tips, handpieces and tubings that can be used. Therefore, in order to estimate the IOP in eye 28, the fluidic resistance must be determined.

Figure 2:
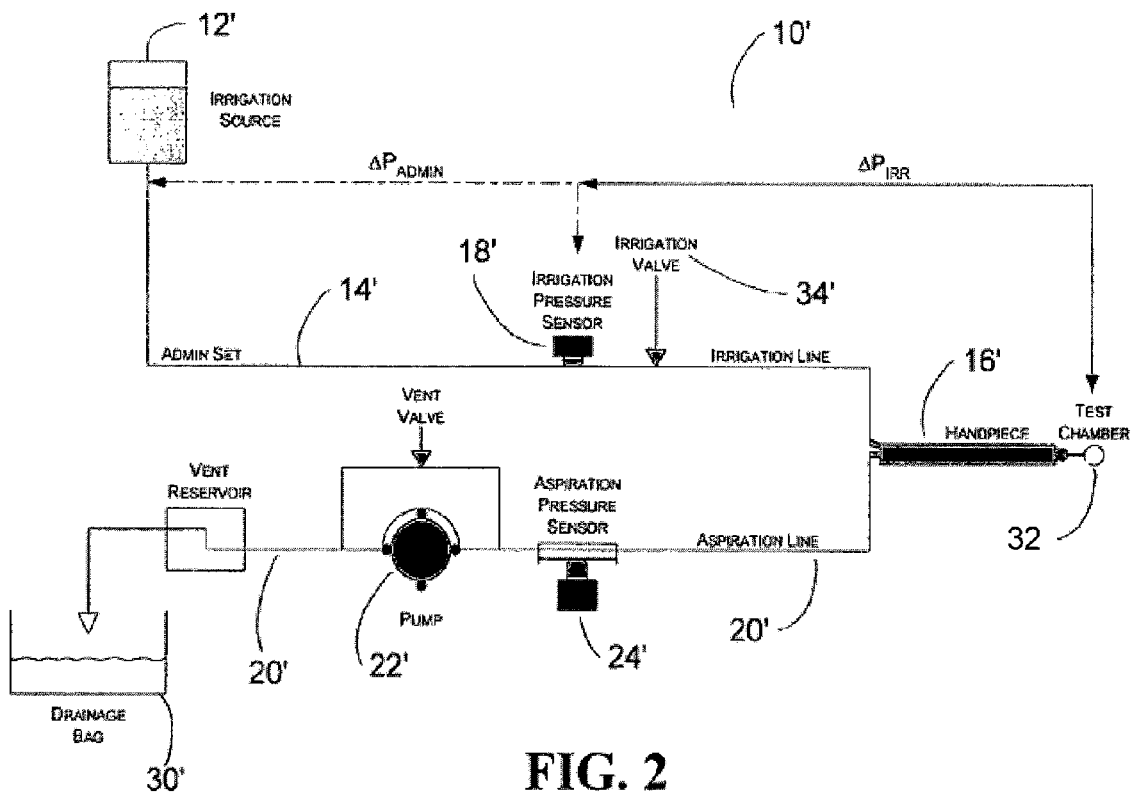
FIG. 2 is a block diagram of one embodiment of a control system that can be used with the method of the present invention during system set-up and priming.
Figure 3:
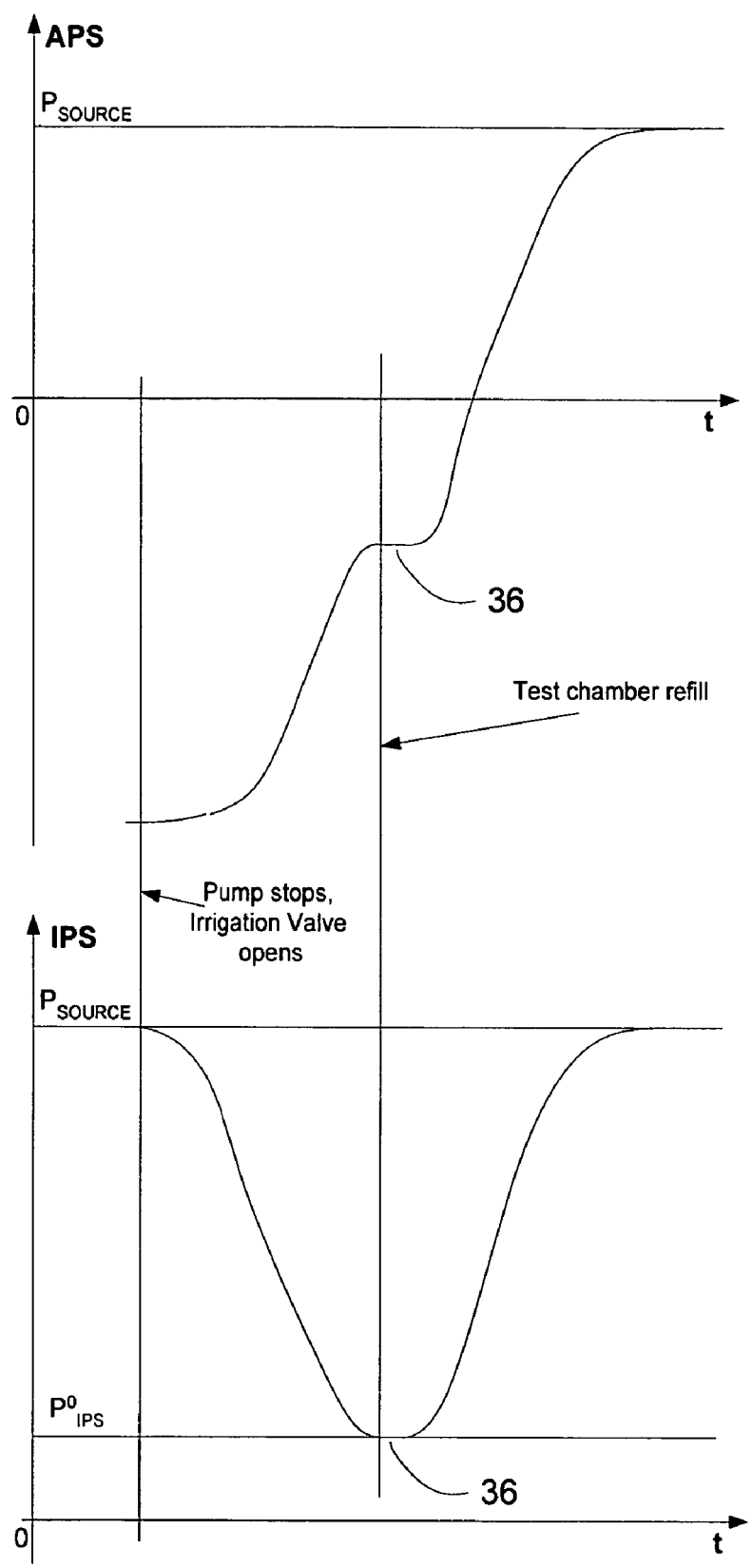
FIG. 3 is a graphical illustration of irrigation and aspiration pressure versus time during the method of the present invention.

As best seen in FIG. 2, system 10' is identical to system 10 illustrated in FIG. 1 except that FIG. 2 represents a surgical system during pre-surgical set-up, or priming, so that test chamber 32 is substituted for eye 28. During the priming operation, a sequence of steps is added to the existing priming steps. Test chamber 32 is evacuated by running pump 22' with irrigation valve 34' closed so that approximately 2-3 cc of fluid is evacuated without pulling a high vacuum in system 10'. At the end of the step test chamber 32 should be collapsed and vacuum in system 10' is approximate 100-150 mm Hg. Pump 22' is stopped and irrigation valve 34' is opened to refill test chamber 32 with irrigation fluid from source 12'. Irrigation and/or aspiration pressure sensors 18' and 24' readings are monitored. When a flat (i.e. test chamber 32 refill) segment is detected in the pressure reading IPS 18' pressure is recorded. FIG. 3 illustrates the pressure curves for both aspiration pressure (vacuum) and irrigation pressure during this step. Flat segment 36 in FIG. 3 illustrated test chamber 32 refill. Flat segment 36 indicates that test chamber 32 pressure (which is the pressure at the handpiece tip 26' as well) is approximately equal to ambient, i.e. 0 mm Hg. Irrigation line 14' resistance ratio ($K_R$) based on the pressure readings is estimated as follows:

$$K_R = \frac{R_{ADMIN}}{R_{IRR}}$$
$$= \frac{\Delta P_{ADMIN}}{\Delta P_{IRR}}$$
$$= \frac{P^0_{SOURCE} - P^0_{IPS}}{P^0_{IPS} - P^0_{TIP}}$$
$$= \frac{P^0_{SOURCE} - P^0_{IPS}}{P^0_{IPS} - 0}$$
$$= \frac{P^0_{SOURCE}}{P^0_{IPS}} - 1$$

Where:

$P^0_{SOURCE}$- irrigation source pressure during the test, $P^0_{IPS}$- IPS reading during the test chamber refill, $P^0_{TIP}$- pressure at the handpiece tip during test chamber refill, $\approx 0$ mm Hg.

During surgery the IOP is estimated based on the current bottle height, current IPS 18 reading, and previously estimated resistance ratio ($K_R$) as follows:

$$P_{IOP} = P_{IPS} - \Delta P_{IRR}$$
$$= P_{IPS} - \frac{\Delta P_{ADMIN}}{K_R}$$
$$= P_{IPS} - \frac{P_{SOURCE} - P_{IPS}}{K_R}$$
$$= \frac{(K_R + 1)P_{IPS} - P_{SOURCE}}{K_R}$$

Where:

$P_{IOP}$-current IOP, $P_{SOURCE}$- current irrigation source pressure, $P_{IPS}$-current IPS reading.

In general, the method utilizes compliance of the test chamber to instrument a transient condition in which the pressure at the handpiece is known, despite the absence of the direct measurement means. The compliance of the test chamber determines the refill pressure at the handpiece during the instrumented condition. For currently used test chambers (highly compliant) the pressure can be accurately assumed to be at ambient (i.e. 0 mmHg). For a lower compliance test chamber, the typical refill pressure value can be accurately established in lab testing.

This description is given for purposes of illustration and explanation. It will be apparent to those skilled in the relevant art that changes and modifications may be made to the invention described above without departing from its scope or spirit.

I claim:

1. A method for determining an irrigation path resistance ratio in an irrigation system having an irrigation pressure sensor, comprising the steps of:
   a) connecting a source of irrigation fluid to a surgical handpiece through an irrigation line, the source of irrigation fluid under control of a surgical system;
   b) connecting a source of aspiration vacuum to the surgical handpiece through an aspiration line, the source of aspiration under the control of the surgical system;
   c) installing a test chamber on the surgical handpiece so as to provide a closed fluid path from the source of irrigation fluid to the source of aspiration vacuum;
   d) exposing the test chamber to a vacuum generated by the source of aspiration vacuum by aspirating a known fluid volume, while closing the irrigation line;
   e) refilling the test chamber by opening the irrigation line;
   f) monitoring a pressure recovery profile in one of the irrigation or aspiration lines;
   g) detecting a characteristic test chamber refill segment in the monitored pressure recovery profile;
   h) determining an irrigation line pressure during the detected test chamber refill segment, as an irrigation pressure sensor (IPS) reading during the refilling of the test chamber;
   i) determining a pressure drop from the source of irrigation fluid to the irrigation pressure sensor during the detected test chamber refill segment;
   j) determining a pressure drop from the irrigation pressure sensor to the test chamber during the detected test chamber refill segment; and
   k) using the pressure drop from the source of irrigation fluid to the irrigation pressure sensor during the detected test chamber refill segment and the pressure drop from the irrigation pressure sensor to the test chamber during the detected test chamber refill segment to determine the irrigation path resistance ratio ($K_R$) of a resistance to irrigation flow from the source of irrigation fluid to the irrigation pressure sensor to a resistance to irrigation flow from the irrigation pressure sensor to the test chamber.

2. The method of claim 1, wherein the resistance ratio $K_R$ is calculated using the following equation:

$$K_R = \frac{R_{ADMIN}}{R_{IRR}}$$
$$= \frac{\Delta P_{ADMIN}}{\Delta P_{IRR}}$$
$$= \frac{P^0_{SOURCE} - P^0_{IPS}}{P^0_{IPS} - P^0_{TIP}}$$
$$= \frac{P^0_{SOURCE} - P^0_{IPS}}{P^0_{IPS} - 0}$$
$$= \frac{P^0_{SOURCE}}{P^0_{IPS}} - 1$$

Where:

$P^0_{SOURCE}$ - irrigation source pressure during the test, $P^0_{IPS}$ - IPS reading during the test chamber refill, $P^0_{TIP}$ - pressure at the handpiece tip during test chamber refill, $\approx 0$ mm Hg.

3. A method for estimating intraocular pressure (IOP) during ophthalmic surgery, comprising the steps of:
   a) connecting a source of irrigation fluid to a surgical handpiece through an irrigation line, the source of irrigation fluid having a pressure under control of a surgical system and a pressure in the irrigation line being monitored by an irrigation pressure sensor (IPS);
   b) connecting a source of aspiration vacuum to the surgical handpiece through an aspiration line, the source of aspiration vacuum under the control of the surgical system;
   c) installing a test chamber on the surgical handpiece so as to provide a closed fluid path from the source of irrigation fluid to the source of aspiration vacuum;
   d) exposing the test chamber to a vacuum generated by the source of aspiration vacuum by aspirating a known fluid volume, while closing the irrigation line;
   e) refilling the test chamber by opening the irrigation line;
   f) monitoring a pressure recovery profile in one of the irrigation or aspiration lines;
   g) detecting a characteristic test chamber refill segment in the monitored pressure recovery profile;
   h) determining an irrigation line pressure during the detected test chamber refill segment as an irrigation pressure sensor reading during the refilling of the test chamber;
   i) determining a pressure drop from the source of irrigation fluid to the irrigation pressure sensor during the detected test chamber refill segment;
   j) determining a pressure drop from the irrigation pressure sensor to the test chamber during the detected test chamber refill segment;
   k) using the pressure drop from the source of irrigation fluid to the irrigation pressure sensor during the detected test chamber refill segment and the pressure drop from the irrigation pressure sensor to the test chamber during the detected test chamber refill segment to determine the irrigation path resistance ratio ($K_R$) of a resistance to irrigation flow from the source of irrigation fluid to the irrigation pressure sensor to a resistance to irrigation flow from the irrigation pressure sensor to the test chamber; and l) estimating the intraocular pressure in an eye during surgery based on the determined irrigation path resistance ratio, the irrigation source pressure and a monitored irrigation pressure sensor reading.

4. The method of claim 3, wherein the resistance ratio $K_R$ is calculated using the following equation:

$$K_R = \frac{R_{ADMIN}}{R_{IRR}}$$
$$= \frac{\Delta P_{ADMIN}}{\Delta P_{IRR}}$$
$$= \frac{P^0_{SOURCE} - P^0_{IPS}}{P^0_{IPS} - P^0_{TIP}}$$
$$= \frac{P^0_{SOURCE} - P^0_{IPS}}{P^0_{IPS} - 0}$$
$$= \frac{P^0_{SOURCE}}{P^0_{IPS}} - 1$$

Where:

$P^0_{SOURCE}$ - irrigation source pressure during the test, $P^0_{IPS}$ - IPS reading during the test chamber refill, $P^0_{TIP}$ - pressure at the handpiece tip during test chamber refill, $\approx 0$ mm Hg.

5. The method of claim 3 wherein the intraocular pressure is estimated using the following equation:

$$P_{IOP} = P_{IPS} - \Delta P_{IRR}$$
$$= P_{IPS} - \frac{\Delta P_{ADMIN}}{K_R}$$
$$= P_{IPS} - \frac{P_{SOURCE} - P_{IPS}}{K_R}$$
$$= \frac{(K_R + 1)P_{IPS} - P_{SOURCE}}{K_R}$$

Where:

$P_{IOP}$ - current IOP, $P_{SOURCE}$ - current irrigation source pressure, $P_{IPS}$ - current IPS reading.

6. An ophthalmic surgical system, comprising:
a surgical handpiece;
a source of irrigation fluid coupled to the surgical handpiece through an irrigation line, wherein the surgical system is configured to control a pressure of the source of irrigation fluid;
an irrigation pressure sensor coupled to the irrigation line, wherein the irrigation pressure sensor is configured to measure a pressure in the irrigation line; and
a source of aspiration vacuum coupled to the surgical handpiece through an aspiration line, wherein the surgical system is configured to control the source of aspiration vacuum;
wherein the surgical system is configured to estimate an intraocular pressure (IOP) in an eye during surgery based on a determined irrigation path resistance ratio of the surgical system, an irrigation source pressure of the source of irrigation fluid, and a monitored irrigation pressure sensor reading from the irrigation pressure sensor.

7. The ophthalmic surgical system of claim 6, wherein the irrigation path resistance ratio is determined during a priming cycle of the surgical system.

8. The ophthalmic surgical system of claim 6, wherein the irrigation path resistance ratio is determined using a test chamber by aspirating the test chamber, refilling the test chamber, detecting a characteristic test chamber refill segment in a monitored pressure recovery profile during the refill, and using a determined pressure drop from the source of irrigation fluid to the irrigation pressure sensor during the detected test chamber refill segment and a determined pressure drop from the irrigation pressure sensor to the test chamber during the detected test chamber refill segment to determine the irrigation path resistance ratio ($K_R$) of a resistance to irrigation flow from the source of irrigation fluid to irrigation pressure sensor to a resistance to irrigation flow from the irrigation pressure sensor to the test chamber.

9. The ophthalmic surgical system of claim 6, wherein the resistance ratio $K_R$ is calculated using the following equation:

$$K_R = \frac{R_{ADMIN}}{R_{IRR}}$$
$$= \frac{\Delta P_{ADMIN}}{\Delta P_{IRR}}$$
$$= \frac{P^0_{SOURCE} - P^0_{IPS}}{P^0_{IPS} - P^0_{TIP}}$$
$$= \frac{P^0_{SOURCE} - P^0_{IPS}}{P^0_{IPS} - 0}$$
$$= \frac{P^0_{SOURCE}}{P^0_{IPS}} - 1$$

Where:

$P^0_{SOURCE}$ - irrigation source pressure during the test, $P^0_{IPS}$ - IPS reading during the test chamber refill, $P^0_{TIP}$ - pressure at the handpiece tip during test chamber refill, $\approx 0$ mm Hg.

10. The ophthalmic surgical system of claim 6, wherein the intraocular pressure is estimated using the following equation:

$$P_{IOP} = P_{IPS} - \Delta P_{IRR}$$
$$= P_{IPS} - \frac{\Delta P_{ADMIN}}{K_R}$$
$$= P_{IPS} - \frac{P_{SOURCE} - P_{IPS}}{K_R}$$
$$= \frac{(K_R + 1)P_{IPS} - P_{SOURCE}}{K_R}$$

Where:

$P_{IOP}$ - current IOP, $P_{SOURCE}$ - current irrigation source pressure, $P_{IPS}$ - current IPS reading.

11. The ophthalmic surgical system of claim 6,
wherein the surgical system further comprises a drainage bag and a pump; and
wherein, during surgery, the surgical handpiece is configured to be held within the eye such that there is continuous fluid communication from the source of irrigation fluid to the drainage bag through the irrigation line, surgical handpiece, aspiration line, and pump.

* * * * *

UNITED STATES PATENT AND TRADEMARK OFFICE
CERTIFICATE OF CORRECTION

PATENT NO. : 7,648,465 B2  Page 1 of 1
APPLICATION NO. : 11/168836
DATED : January 19, 2010
INVENTOR(S) : Raphael Gordon It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1155 days.

Signed and Sealed this

Twenty-third Day of November, 2010

David J. Kappos
*Director of the United States Patent and Trademark Office*